United States Patent
Mulier et al.

[11] Patent Number: 5,980,516
[45] Date of Patent: *Nov. 9, 1999

[54] METHOD AND APPARATUS FOR R-F ABLATION

[75] Inventors: Peter M. J. Mulier, St. Paul; Michael F Hoey, Shoreview, both of Minn.

[73] Assignee: Medtronic, Inc., Minneapolis, Minn.

[ * ] Notice: This patent is subject to a terminal disclaimer.

[21] Appl. No.: 09/037,725

[22] Filed: Mar. 9, 1998

Related U.S. Application Data

[63] Continuation of application No. 08/946,942, Oct. 9, 1997, which is a continuation of application No. 08/424,681, Apr. 18, 1995, abandoned, which is a continuation of application No. 08/113,441, Aug. 27, 1993, Pat. No. 5,431,649.

[51] Int. Cl.$^6$ ..................................................... A61B 17/39
[52] U.S. Cl. .......................... 606/41; 604/264; 604/272; 607/104
[58] Field of Search .......................... 606/41, 42, 45–50; 607/100–105, 115, 116, 122, 127; 604/21, 22, 264, 272

[56] References Cited

U.S. PATENT DOCUMENTS

| | | |
|---|---|---|
| 4,026,301 | 5/1977 | Friedman et al. . |
| 4,564,054 | 1/1986 | Gustavason . |
| 4,674,499 | 6/1987 | Pao . |
| 4,799,495 | 1/1989 | Hawkins et al. . |
| 4,886,060 | 12/1989 | Wiksell . |
| 5,002,067 | 3/1991 | Berthelsen et al. . |
| 5,003,990 | 4/1991 | Osypka . |
| 5,003,992 | 4/1991 | Holleman et al. . |
| 5,030,204 | 7/1991 | Badger et al. . |
| 5,060,660 | 10/1991 | Gambale et al. . |
| 5,083,565 | 1/1992 | Parins . |
| 5,104,393 | 4/1992 | Isner et al. . |
| 5,122,137 | 6/1992 | Lennox . |
| 5,122,138 | 6/1992 | Manwaring . |
| 5,165,421 | 11/1992 | Fleischhacker et al. . |
| 5,246,014 | 9/1993 | Williams et al. . |
| 5,281,218 | 1/1994 | Imran . |
| 5,353,800 | 10/1994 | Pohndorf et al. . |
| 5,403,311 | 4/1995 | Abele et al. . |
| 5,431,649 | 7/1995 | Mulier et al. . |
| 5,433,708 | 7/1995 | Nichols et al. . |
| 5,437,660 | 8/1995 | Johnson et al. . |
| 5,454,807 | 10/1995 | Lennox et al. . |
| 5,542,944 | 8/1996 | Bhatta . |

FOREIGN PATENT DOCUMENTS 9304722  3/1993  WIPO .

OTHER PUBLICATIONS

Clinical Research Abstract "Human and Canine Pathological Transmural Myocardial Radiofrequency Ablation Lesions" by Nolasco, May 4–5, 1993, San Diego, CA.

*Primary Examiner*—Michael Peffley
*Attorney, Agent, or Firm*—Reed A. Duthler; Harold R. Patton

[57] ABSTRACT

An ablation catheter and a method of performing cardiac ablation. The catheter is provided with a hollow, helical electrode, which is screwed into cardiac tissue at a desired ablation site and connected to a source of R-F electrical energy to ablate the tissue adjacent the electrode. Prior to ablation, a conductive fluid may be injected through the hollow needle, both to provide for cooling of the tissue adjacent the needle and to increase the conductivity of the tissue in the area of the electrode.

13 Claims, 3 Drawing Sheets

METHOD AND APPARATUS FOR R-F ABLATION

This application is a continuation of application Ser. No. 08/946,942 filed Oct. 9, 1997 which is a continuation application of Ser. No. 08/424,681 filed Apr. 18, 1995 (abandoned) which is a continuation application of Ser. No. 08/113,441 filed Aug. 27, 1993 now U.S. Pat. No. 5,431,649.

BACKGROUND OF THE INVENTION

This invention relates generally to the field of devices for cardiac surgery, and more specifically to devices for R-F ablation of cardiac tissue.

The present invention is directed toward treatment of tachyarrhythmias, which are heart rhythms in which an chamber or chamber of the heart exhibits an excessively fast rhythm. In particular, the present invention is directed toward treatment of tachycardias, which are due to the presence of ectopic foci within the cardiac tissue or due to the presence of aberrant condition pathways within the cardiac tissue.

Therapies have been developed for treating tachycardias by destroying cardiac tissue containing identified ectopic foci or aberrant conduction pathways. A variety of approaches have been taken, including application of electrical energy or other forms of energy to destroy the undesired cardiac tissue. As examples, ablation of cardiac tissue has been accomplished by means of radio frequency electrical current, microwave energy, heat, electrical pulses, cryothermy, and lasers. At present, ablation using R-F energy is perhaps the most widely practiced in the context of ablation procedures that can be carried out by means of a catheter, inserted into the closed heart.

Most R-F ablation catheters employ electrodes which are intended to contact the endocardium of the heart, or, in some cases as in U.S. Pat. No. 5,083,565, are intended to penetrate the endocardium, and enter the myocardium. In general, R-F ablation catheters are effective to induce small lesions in heart tissue including the endocardium and inner layers of myocardium, in the immediate vicinity of the electrode. However, the medical community has expressed a desire for devices which produce larger lesions, to reduce the number of applications of R-F energy (burns) required to effectively ablate the cardiac tissue associated with the tachycardia.

R-F ablation causes tissue in contact with the electrode to heat through resistance of the tissue to the induced electrical current therethrough. The actual extent of heating is somewhat unpredictable. However, temperature tends to rise as the duration and amplitude of the R-F signal increase. Heating of the tissue beyond a certain point can cause dissection or charring of the tissue, resulting in a high impedance between the R-F electrode and the return electrode, which in turn leads to cessation of the heating process, and, in some cases, sticking of the electrode to the charred tissue. One response to this phenomenon has been the inclusion of thermocouple within the ablation electrode, in conjunction with feedback control to modulate the R-F signal to maintain the electrode temperature at a set parameter. One such system is disclosed in U.S. Pat. No. 5,122,137.

SUMMARY OF THE INVENTION

The present invention is directed toward improving the consistency and efficacy of R-F ablation, and to increase the overall size and extent of the lesions induced by R-F ablation. These goals are pursued by means of an ablation catheter employing a helical electrode intended to be screwed into the myocardium at the site intended for ablation. The helical electrode provides an enlarged surface are as compared to relatively straight or needle-like electrodes for insertion into the endocardium, and also serves to stabilize the location of the catheter during the application of the R-F signal. In addition, there is essentially no bleeding following removal of the helical electrode, so it can safely be placed in multiple locations for mapping and ablation purposes.

An additional aspect of the invention in its preferred embodiment is the provision of a non-toxic, non-arrhythmogenic, conductive solution such as Ringer's solution to the area of the electrode, before and during application of R-F energy. In its preferred embodiment, the helical electrode is hollow, and the conductive solution is applied through one or more apertures in the electrode. The conductive solution injected prior to application of the R-F signal is believed to displace blood in the vicinity of the electrode. Ringer's solution, for example, has a much higher conductivity than blood (approximately 3–4x) or cardiac muscle (approximately 7x), overall resistance to the induced electrical current is reduced, which is believed to assist in expanding the size of the lesion, by spreading the effective area of application of the electrical current over a wider area. Application of the conductive solution during the burn further assists by preventing overheating of the tissue, allowing for a prolonged application of the R-F signal, extending beyond the point at which burning or charring would otherwise normally occur. Both of these factors are believed to contribute to an increase in the overall size of the lesion produced by application of R-F energy at a particular location.

DETAILED DESCRIPTION OF THE PREFERRED EMBODIMENTS

Figure 1:
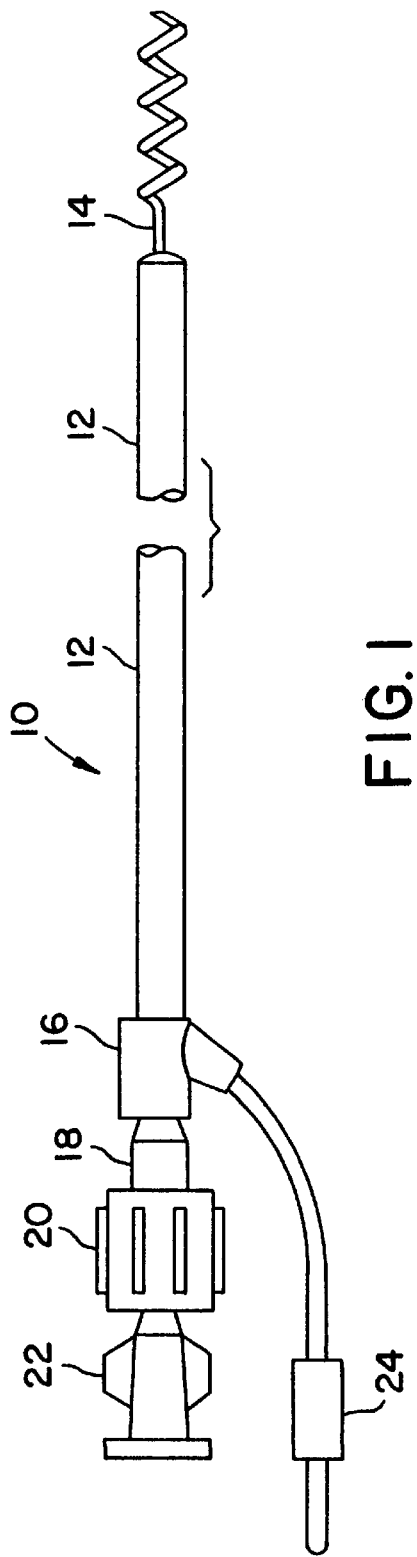
FIG. 1 is a plan view of a catheter adapted to perform the improved method of R-F ablation, according to the present invention.

FIG. 1 is a plan view of a catheter specifically designed for performing R-F ablation according to the present invention. The catheter includes an elongated catheter body 10, comprising an insulative outer sheath 12, which may be made of polyurethane, teflon, or other biocompatible plastic. A hollow, helical electrode 14 is located at the distal end of the catheter and is coupled to the distal end of an internal tube, running the length of the catheter. At the proximal end of the catheter a fitting 16 is located, to which luer lock 18 is coupled. Luer lock 18 is coupled to the proximal end of the internal tube. A swivel mount 20 is mounted to luer lock 18, allowing rotation of the catheter relative to luer lock 22. Luer lock 22 is intended to be coupled to a source of conductive fluid such as Ringer's solution, and allows for application of the Ringer's solution through the catheter and through electrode 14, while electrode 14 is being screwed into heart tissue. An electrical connector 24 exits fitting 16, and is coupled to electrode 14, allowing for the use of electrode 14 to apply R-F energy to heart tissue. Electrode 14 may also be employed for other related functions such as measurement of electrograms within the heart and pacing of heart tissue by application of low energy pulses appropriate for cardiac pacing. In use, the catheter is advanced to the desired site for ablation, which preferably has been previously identified by means of cardiac mapping in a fashion similar to cardiac mapping presently employed with R-F ablation procedures. The catheter may be guided to the desired location by being passed down a steerable or guidable catheter, for example, as disclosed in U.S. Pat. No. 5,030,204, issued to Badger et al., or by means of a fixed configuration guide catheter, for example in U.S. Pat. No. 5,104,393, issued to Isner, both of which patents are incorporated herein by reference in their entireties. Alternatively, the catheter may be advanced to the desired site within a heart by means of a deflectable stylet, as disclosed in PCT Patent Application WO 93/04724, published Mar. 18, 1993, or a deflectable guidewire as disclosed in U.S. Pat. No. 5,060,660, issued to Gambale, et al., both of which patents are incorporated herein by reference in their entireties. When the hollow needle 14 is located at the desired location it is screwed into heart tissue by rotating the catheter body. A torque cable within the catheter body provides for 1:1 torque transfer from the proximal end of the catheter to the hollow needle 14.

When advanced to the desired location, luer lock 22 is coupled to a pressurized source of Ringer's solution. An appropriate source is discussed in more detail in conjunction with FIG. 6 below. However, for purposes of the present invention, a source of Ringer's solution capable of delivering 1 cc per minute of solution at atmospheric pressure has been found to be adequate. Delivery of Ringer's solution should begin before or at the time at which the electrode 14 is screwed into the tissue to be ablated. In animal experimentation, the inventors have found that delivery of Ringer's solution for a period of two minutes prior to the delivery of R-F energy assists in producing a larger but still controlled, regular lesion.

After the electrode has been located, and Ringer's solution has been administered for the desired period of time, electrical connector 24 is coupled to an R-F electrosurgical power source, of the type commercially available and employed for cutting an electro-coagulation. The present inventors have employed a Blendtome brand electrosurgical generator, Model No. 755, coagulation setting number 7, cutting setting number 1. At these settings, a prolonged application of R-F energy, e.g., one minute or so, may be employed to produce a large, controlled lesion. Greater or lesser time periods may be employed, however, time periods less than 20 seconds may be counter-indicated, as it appears that the cooling effect of the Ringer's solution, in such shorter R-F application times, may actually decrease the effective size of the lesion.

After R-F ablation, the electrode 14 may be coupled to a cardiac pacemaker, and cardiac pacing energy may be delivered to the lesion site in an attempt to measure the pacing threshold. Pacing threshold may be measured by delivering pacing pulses at differing energy levels, e.g. by altering pulse amplitude or width, and determining the minimum energy level effective to cause a depolarization of cardiac tissue. The inventors believe that the higher the pacing threshold, assuming a relatively homogenous lesion, the greater lesion size. As such, the electrode 14 can be used to derive a rough estimate of overall lesion size. The electrode 14 may also be coupled EKG monitoring equipment to assist in determining whether the tachycardia persists and whether the tissue in the vicinity of the electrode is still participating in aberrant conduction or ectopic activity, associated with the tachycardia.

The helical configuration of electrode 14 is believed to be particularly beneficial in the context of an ablation electrode. Because the electrode is screwed into and completely located within the heart tissue, out of the bloodstream, application of R-F energy is limited to the tissue itself. This differs from traditional R-F ablation electrodes, which simply contact the endocardium, with the result that a substantial portion of the energy applied is dissipated in the blood within the heart adjacent the electrode site. Moreover, R-F energy applied to the bloodstream may cause clotting of the blood adjacent the electrode, and raise the risk of clots breaking loose of the electrode.

The helical electrode also provides a substantially increased surface area as compared to the needle-like electrodes proposed in the above cited Parins patent, and also serves to anchor the catheter reliably during application of the R-F energy. In addition, the helical shape of the electrode prevents the application of conductive solution through the electrode from causing the electrode to be backed out of its insertion site due to hydraulic pressure, as might occur if a straight, hollow electrode were employed. The elongated path defined by the helical electrode also reduces the possibility of leakage of conductive fluid along the needle and out of the heart tissue.

Figure 2:
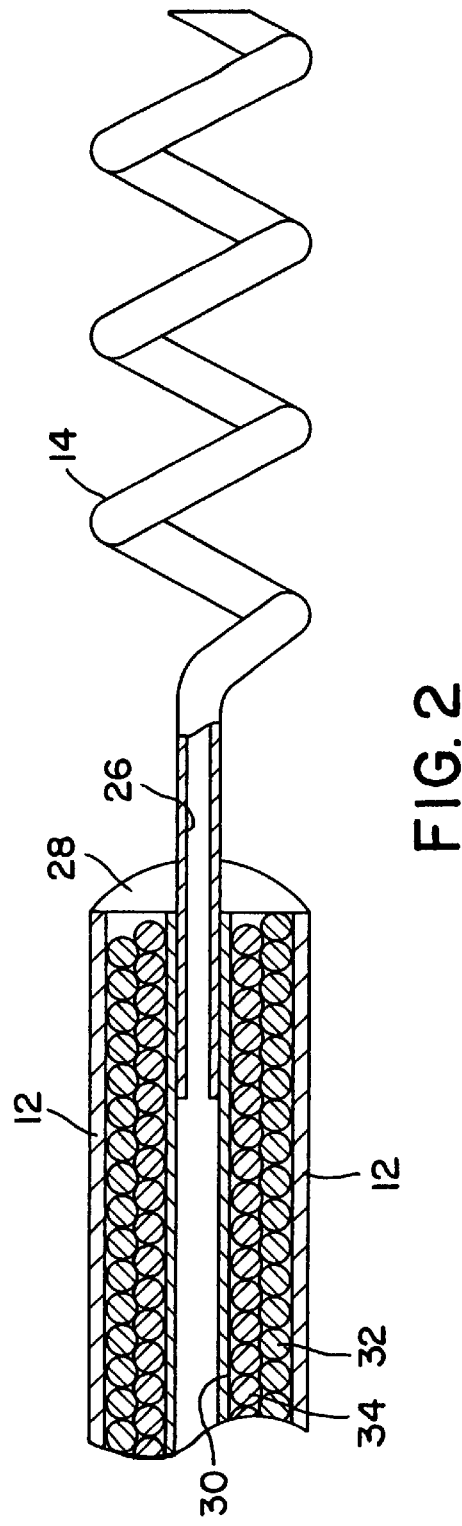
FIG. 2 is a cutaway view through the distal end of the catheter illustrated in FIG. 1.

FIG. 2 illustrates a cutaway version through the end of the catheter illustrated in FIG. 1. In this view, it can be seen that helical electrode 14 is provided with an internal lumen 26 which is in communication with the internal lumen of a tube 30. Tube 30 extends to the proximal end of the catheter and is in full communication with luer lock 18, as discussed above, tube 30 may be fabricated of polyimide tubing or of stainless steel tubing. In the present invention, the stainless steel tubing serves as an additional conductor, coupling electrode 14 to electrical connector 24 and enhancing the overall conductivity of the catheter. The use of polyimide tubing, while reducing the overall conductivity of the catheter enhances the flexibility somewhat, and may be beneficial in some cases. It is recommended to apply a steady flow of Ringer's solution through the tubing to electrode 14 during passage catheter through the vascular system to the electrode site, if possible. The flow of Ringer's solution in this case assists in maintaining the patency of the lumen of tubing 30, and prevents plugging of the exit ports of the electrode as it is advanced into the cardiac muscle.

Surrounding tube 30 are two coils 32 and 34, which are wound in opposite directions, to provide a torque cable. In the case of the specific devices employed by the inventors, a torque cable as manufactured by Lake Region Manufacturing Company of Chaska, Minn. was employed, which torque cable is described in U.S. Pat. No. 5,165,421, incorporated herein by reference in its entirety. Coils 32 and 34 also serve as conductors. As illustrated, tubing 30 is between metal coils 32 and 34 and helical electrode 14. However, if polyimide tubing is used, the coils 32 and 34 will serve as the only conductor and thus will be electrically coupled to electrode 14 by means of welding, soldering or mechanical interconnection. Insulative sleeve 12 serves both to provide a smooth exterior for the catheter and to insulate the metal coils 32 and 34, along the length of the catheter.

Figure 3:
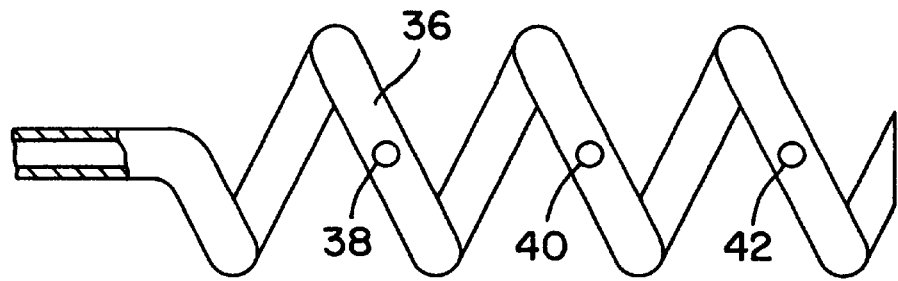
FIGS. 3, 4, and 5 illustrate alternative embodiments of the helical electrode of the catheter illustrated in FIGS. 1 and 2.
Figure 4:
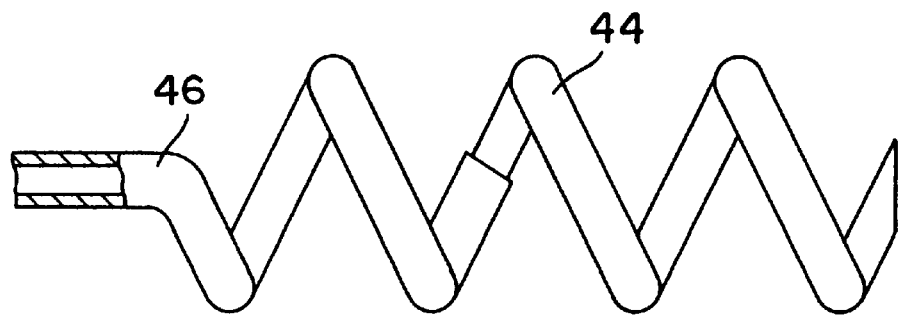
Figure 5:
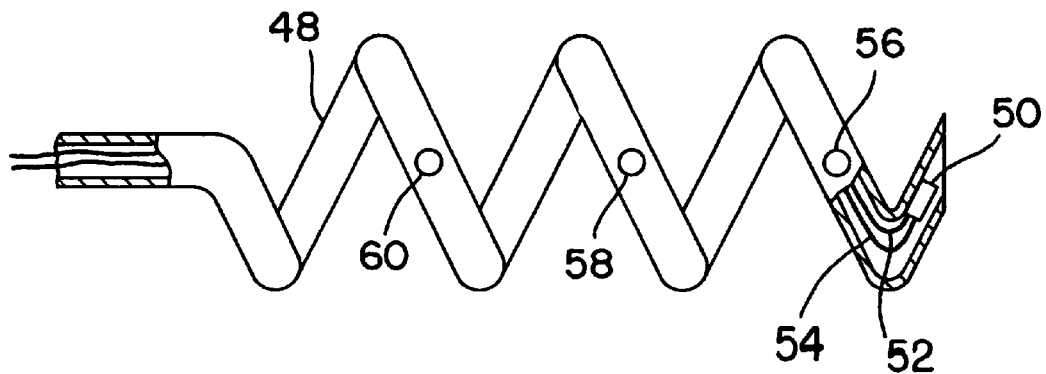

FIGS. 3, 4 and 5 illustrate alternate embodiments of the helical electrode illustrated in FIG. 2. The electrode in FIG. 2 comprises a hollow tube having a single exit port located as its distal end. Electrode 36, illustrated in FIG. 3, corresponds to electrode 14 with the exception that additional exit ports 38, 40 and 42 have been added, allowing for dispensing of the Ringer's solution along the length of the helix. Ports 38, 40 and 42 may be laser drilled, and may be spaced in any desired fashion around the circumference of electrode 36 and along the length of electrode 36. Preferably, it is believed desirable to have ports spaced around the full circumference of the electrode, to provide for an even dispensing and dispersing of Ringer's solution.

Electrode 44, illustrated in FIG. 4 is a second alternative embodiment of a helical electrode corresponding to electrode 14, but with the addition of an insulative sleeve 46, which covers the proximal portion of the electrode. Sleeve 46 limits the application of R-F energy to the distal portion of the electrode. Optionally, additional exit ports corresponding to ports 38, 40 and 42 illustrated in FIG. 43 may also be employed in conjunction with electrode 44. These additional exit ports may be limited to the exposed, uninsulated portion of electrode 44, or may extend along the entire length of electrode 44.

Electrode 48, illustrated in FIG. 5 is a third alternative embodiment corresponding generally to electrode 14. However, in this case, electrode 48 is provided with a thermocouple 50 located in the distal end of electrode 48. Thermocouple wires 52 and 54 extend backwards through the lumen within electrode 48 and are used to monitor the temperature at the tip of the electrode, for use in feedback control of power applied to the electrode as described in the above-cited patent issued to Lennox et al. Only one of thermocouple wires 54 and 52 is insulated, and the other is simply coupled to the interior of electrode 48. In order to employ the electrode of FIG. 4B, an additional electrical connector would have to be added to the embodiment illustrated in FIG. 5, in order to allow connection to the thermocouple wire not connected to electrode 48. Alternatively, both thermocouple wires may be insulated, requiring two additional electrical connectors at the proximal end of the device, each coupled to one of the thermocouple wires. It should be noted that the thermocouple 50 effectively blocks the distal opening of the lumen within electrode 48, so that Ringer's solution will be dispensed only by means of side ports 56, 58 and 60.

Figure 6:
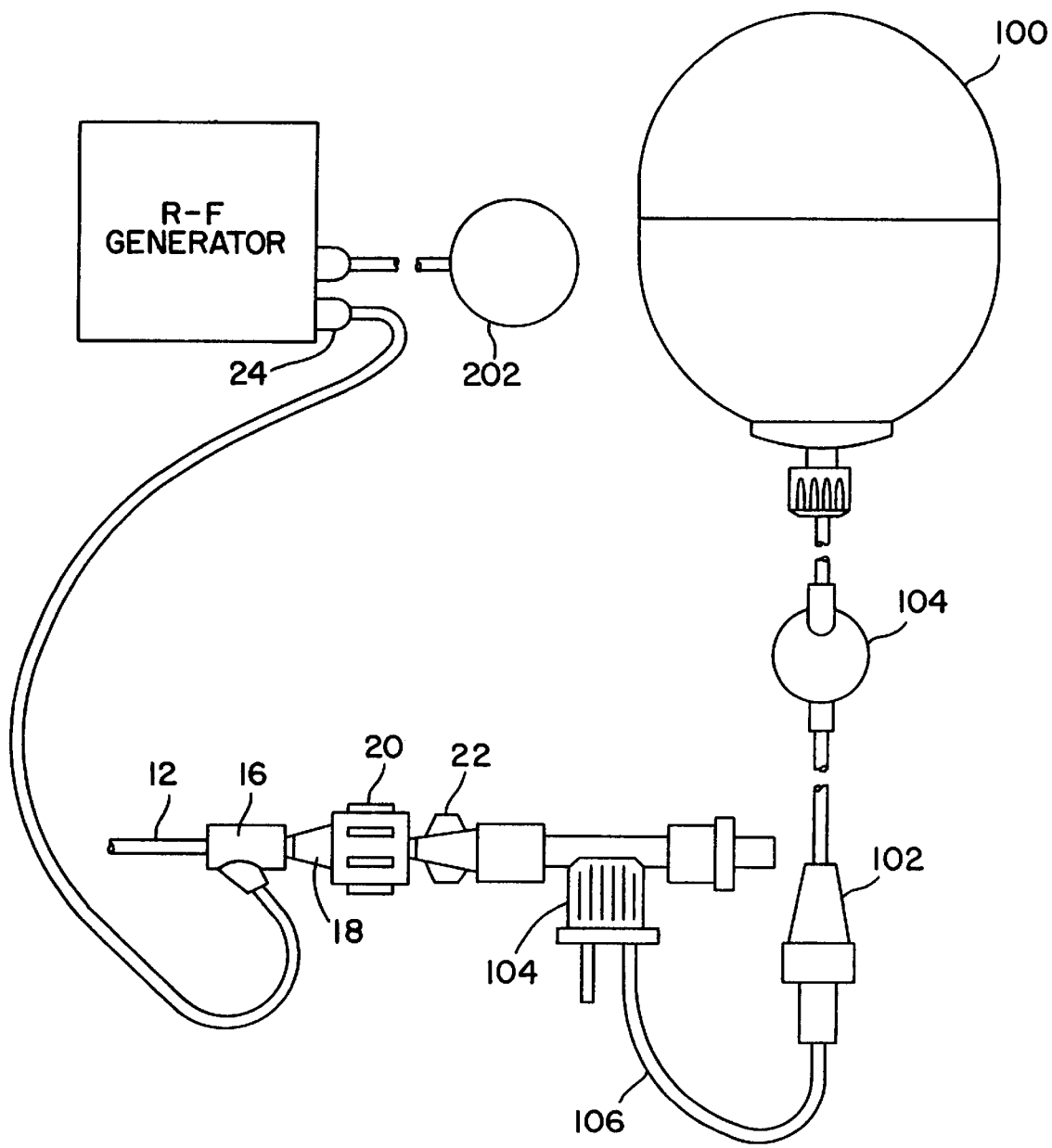
FIG. 6 illustrates the associated apparatus for administration of conductive solution before and during application of R-F energy to the helical electrode.

FIG. 6 illustrates a pressurized source for Ringer's solution which may be employed in conjunction with catheter illustrated in FIG. 1. A reservoir 100 is provided, which is commercially manufactured by Block Medical Inc., and sold under the brand name "Home Pump". The reservoir contains Ringer's solution and provides Ringer's solution at one atmosphere pressure to flow control 102, via filter 104. Flow control 102 may, for example, provide a flow limit of 20 drops or 1 cc per minute. Flow control 102 is coupled to a second flow control element 104, which, in the experimental apparatus employed by the inventors allows for additional adjustability of flow rates. Flow control 104 is coupled to the luer lock 22, illustrated in FIG. 1, which in turn is in fluid communication with electrode 14 (FIG. 1), allowing delivery of Ringer's solution to the electrode. An electrosurgical generator 200 for providing R-F electrical energy is illustrated in functional block form, coupled to electrical connector 24 and to a ground plate electrode 202 (not drawn to scale). All other labeled elements correspond to those illustrated in FIG. 1.

Wile the embodiment illustrated above requires a second element (e.g. a guide catheter or guide wire) for advancing and positioning the catheter at its desired location, it is anticipated that the basic apparatus disclosed above may also be incorporated into catheters which themselves are steerable or deflectable, similar to R-F ablation catheters presently in clinical investigation. Similarly, it is anticipated that in commercial embodiments, alternative mechanisms (e.g. precision pumps) for controlling the flow of Ringer's solution may be employed. Similarly, while the inventors have employed Ringer's solution, other alternative fluids may be workable as well. As such, the embodiment discussed above should be considered exemplary, rather than limiting, in conjunction with the following claims.

In conjunction with the above specification, we claim:

1. A catheter system, comprising a catheter and a fluid reservoir, wherein said catheter comprises:

a catheter body proximal end, a distal end, an internal longitudinal lumen;

a hollow helical needle mounted to the distal end of said catheter body, in fluid communication with said longitudinal lumen; and a fluid coupling mounted to the proximal end of the catheter body, in fluid communication with said longitudinal lumen; and wherein said fluid reservoir is coupled to said fluid coupling whereby fluid in said reservoir can be delivered through said hollow helical needle.

2. A system according to claim 1 further comprising means for regulating flow from said reservoir to said hollow helical needle.

3. A system according to claim 1 or claim 2 wherein said reservoir contains a saline solution.

4. A system according to claim 3 wherein said catheter body further comprises an electrical conductor, coupled to said hollow helical needle.

5. A system according to claim 1 or claim 2 wherein said reservoir contains a conductive fluid.

6. A system according to claim 5 wherein said catheter body further comprises an electrical conductor, coupled to said hollow helical needle and extending proximally therefrom in said catheter body.

7. A system according to claim 1 or claim 2 wherein said catheter body comprises a torque transfer member, coupled to said hollow helical needle.

8. A system according to claim 7 wherein said torque transfer member comprises a torque cable, coupled to said hollow helical needle and extending proximally therefrom in said catheter body.

9. A system according to claim 7 wherein said torque transfer member is coupled to the proximal end of the catheter body.

10. A system according to claim 7 wherein said torque transfer member is fabricated of a conductive material.

11. A system according to claim 7 wherein said reservoir contains a conductive solution.

12. A system according to claim 11 wherein said catheter body further comprises an electrical conductor coupled to said hollow helical needle and extending proximally therefrom in said catheter body.

13. A system according to claim 7 wherein said reservoir contains a saline solution.

\* \* \* \* \*